United States Patent
Do et al.

(10) Patent No.: US 11,491,203 B2
(45) Date of Patent: Nov. 8, 2022

(54) NUTRACEUTICALS SUPPLEMENT COMPOSITION FOR REGULATING METABOLISM AND ANTI-AGING

(71) Applicant: Viva Life Science, Inc., Costa Mesa, CA (US)

(72) Inventors: Thuong Cao Do, Westminster, CA (US); Ping Yang, Fountain Valley, CA (US)

(73) Assignee: VIVA LIFE SCIENCE, INC., Costa Mesa, CA (US)

( * ) Notice: Subject to any disclaimer, the term of this patent is extended or adjusted under 35 U.S.C. 154(b) by 52 days.

(21) Appl. No.: 17/203,558

(22) Filed: Mar. 16, 2021

(65) Prior Publication Data

US 2021/0290722 A1 Sep. 23, 2021

Related U.S. Application Data

(60) Provisional application No. 62/990,855, filed on Mar. 17, 2020.

(51) Int. Cl.

| | |
|---|---|
| *A61K 36/9068* | (2006.01) |
| *A61K 36/48* | (2006.01) |
| *A61K 36/38* | (2006.01) |
| *A61K 36/77* | (2006.01) |
| *A61K 31/14* | (2006.01) |
| *A61K 36/288* | (2006.01) |
| *A61K 36/67* | (2006.01) |
| *A61K 36/236* | (2006.01) |
| *A61K 36/06* | (2006.01) |
| *A61K 45/06* | (2006.01) |
| *A23L 33/00* | (2016.01) |
| *A61K 36/738* | (2006.01) |
| *A61K 36/258* | (2006.01) |
| *A61K 36/8962* | (2006.01) |
| *A61K 9/20* | (2006.01) |
| *A61K 9/16* | (2006.01) |
| *A61K 9/48* | (2006.01) |
| *A61K 36/74* | (2006.01) |
| *A61K 36/24* | (2006.01) |
| *A61K 36/87* | (2006.01) |
| *A61K 36/82* | (2006.01) |
| *A23L 33/105* | (2016.01) |

(52) U.S. Cl.
CPC .......... *A61K 36/9068* (2013.01); *A23L 33/30* (2016.08); *A61K 9/16* (2013.01); *A61K 9/20* (2013.01); *A61K 9/48* (2013.01); *A61K 31/14* (2013.01); *A61K 36/06* (2013.01); *A61K 36/236* (2013.01); *A61K 36/24* (2013.01); *A61K 36/258* (2013.01); *A61K 36/288* (2013.01); *A61K 36/38* (2013.01); *A61K 36/48* (2013.01); *A61K 36/67* (2013.01); *A61K 36/738* (2013.01); *A61K 36/74* (2013.01); *A61K 36/77* (2013.01); *A61K 36/82* (2013.01); *A61K 36/87* (2013.01); *A61K 36/8962* (2013.01); *A61K 45/06* (2013.01); *A23L 33/105* (2016.08)

(58) Field of Classification Search
None
See application file for complete search history.

(56) References Cited

U.S. PATENT DOCUMENTS

| | | | |
|---|---|---|---|
| 7,579,027 | B2 | 8/2009 | Birketvedt |
| 8,563,051 | B2 | 10/2013 | Samuel et al. |
| 8,974,841 | B2 | 3/2015 | Qu |
| 9,931,316 | B2 | 4/2018 | Stamets |
| 2004/0001817 | A1 | 1/2004 | Giampapa et al. |
| 2005/0003027 | A1 | 1/2005 | Diaz et al. |
| 2006/0024385 | A1 | 2/2006 | Pedersen |
| 2008/0305096 | A1 | 12/2008 | Vedegem et al. |
| 2009/0252796 | A1 | 10/2009 | Mazed |

FOREIGN PATENT DOCUMENTS

EP 2617429 A1 7/2013

OTHER PUBLICATIONS

"List of vitamins", Harvard Medical School. Updated: Nov. 14, 2018, Jun. 2009.
ASL, Marjan Nassiri, et al., "Review of Pharmacological Effects of *Glycyrrhiza* sp. and its Bioactive Compounds", Phytotherapy Research vol. 22, Issue6, Jun. 2008, pp. 709-724.
ASL, Marjan Nassiri, et al., "Review of the pharmacological effects of *Vitis vinifera* (Grape) and its bioactive constituents: An Update", Phytotherapy Research 30, May 16, 2016, pp. 1392-1403.
Badoni, Ruchi, et al., "A comprehensive scientific overview of Garcinia cambogia", Fitoterapia, vol. 102, Apr. 2015, pp. 134-148.

(Continued)

*Primary Examiner* — Aaron J Kosar
(74) *Attorney, Agent, or Firm* — Kurt T. Mulville; VLP Law Group LLP

(57) ABSTRACT

Nutraceuticals Composition A (metabolic capacity enhancing compositions) comprises extraction or powder from White Kidney Bean, Green Tea, Green Coffee Bean, *Garcinia Cambogia*, Gymnema *Sylvestre*, L-Carnitine, Guarana, Ginger Root, Dandelion Root, *Capsicum* Cayenne, Licorice Root, Ascorbic Acid, d-Calcium Pantothenate, Pyridoxine HCl, Potassium Chloride, Magnesium Carbonate, and Chromium Yeast. Nutraceuticals Composition B (immunity capacity enhancing compositions) comprises extraction or powder from Grape Seed, *Ginseng*, Garlic, Rosehips, Green tea (Decaf), *Astragalus*, *Beta* Glucan Yeast, Reishi, Shitake, Maitake, Agricus blazei, Turkey Tail, *Cordyceps*, and Coenzyme CoQ10. The methods to make a synergistic Composition A and Composition B are formulated and are capable to provide a bioavailable dietary supplement and phytonutrients that can help modulate metabolism and enhance the human immune system. The supplementation, consumption, of these nutraceutical formulas have preventive and therapeutic roles for chronic diseases, and thus provide anti-aging effects.

20 Claims, 2 Drawing Sheets

(56) References Cited

OTHER PUBLICATIONS

Bayan, Leyla, et al., "Garlic: a review of potential therapeutic effects", Avicenna J Phytomed 4(1), Jan.-Feb. 2014, pp. 1-14.

Block, Keith I., et al., "Immune system effects of echinacea, ginseng, and astragalus: a review", Integr Cancer Ther. 2(3), 2003, pp. 247-267.

Bulku, Elida, et al., "A novel dietary supplement containing multiple phytochemicals and vitamins elevates hepatorenal and cardiac antioxidant enzymes in the absence of significant serum chemistry and genomic changes", Oxidative Med and Cellular Longevity, 3:2, Landes Bioscience, Mar. 2010, pp. 129-144.

Chaiyasit, Kamon, "Pharmacokinetic and The Effect of Capsaicin in Capsicum frutescens on Decreasing Plasma Glucose Level", J Med Assoc Thai, vol. 92, No. 1, 2009, pp. 108-113.

Cheung, Nai-Kong V., et al., "Orally administered beta-glucans enhance anti-tumor effects of monoclonal antibodies", Cancer Immunol Immunother. 51(10) Epub PMID: 12384807, Nov. 2002, pp. 1-5.

Choi, Ung-Kyu, et al., "Hypolipidemic and Antioxidant Effects of Dandelion (*Taraxacum officinale*) Root and Leaf on Cholesterol-Fed Rabbits", Int J Mol Sci, v.11 (1), Jan. 2010, pp. 67-78.

Cooper, Raymond, et al., "Medicinal Benefits of Green Tea: Part I. Review of Noncancer Health Benefits", The Journal of Alternative and Complementary Medicine vol. 11, No. 3., Nov. 3, 2005, pp. 521-528.

Goa, Karen L., et al., "L-Carnitine A Preliminary Review of its Pharmacokinetics, and its Therapeutic Use in Ischaemic Cardiac Disease and Primary and Secondary Carnitine Deficiencies in Relationship to its Role in Fatty Acid Metabolism", Drugs vol. 34, Oct. 23, 2012, pp. 1-24.

González-Castejón, Marta, et al., "Diverse biological activities of dandelion", Nutrition Reviews, vol. 70, Issue 9,, Sep. 1, 2012, pp. 534 547.

Guo, Cuixia, et al., "Mushroom and Immunity", Current Topics in Nutraceutical Research. vol. 10, No. 1, 2012, pp. 31-42.

Hamerski, Lidihone, et al., "Paullinia cupana Kunth (Sapindaceae): A review of its ethnopharmacology, phytochemistry and pharmacology", Journal of Medicinal Plants Research Review. vol. 7(30), Aug. 10, 2013, pp. 2221-2229.

Khan, Ahmadi M., et al., "A Review on Medicinal Plant of *Glycyrrhiza glabra* L.", Journal of Medicinal Plants, vol. 12, No. 46, May 2013, pp. 1-12.

Kim, Yun Jung, et al., "A mixture of the aqueous extract of Garcinia cambogia, soy peptide and L-carnitine reduces the accumulation of visceral fat mass in rats rendered obese by a high fat diet", Genes & Nutrition vol. 2, Nov. 17, 2007, pp. 353-358.

Kim, Jisu, et al., "Nutrition Supplements to Stimulate Lipolysis: A Review in Relation to Endurance Exercise Capacity", J of Nutritional Science and Vitaminology 62, 2016, pp. 141-161.

Krewer, Cristina Da Costa, et al., "Habitual Intake of Guarana and Metabolic Morbidities: An Epidemiological Study of an Elderly Amazonian Population", Phytother. Res. vol. 25, issue 9, abstract, Feb. 22, 2011, 1 page.

Leung, Kar Wah, et al., "Pharmacology of ginsenosides: a literature review", Chinese Medicine vol. 5, Article No. 20, 2010, pp. 1-7.

Mau, Jeng-Leun, et al., "Antioxidant properties of several medicinal mushrooms", J Agric Food Chem. 50 (21), Oct. 9, 2002, pp. 6072-6077.

Moghaddasi, Mohammad Sharrif, et al., "Ginger (*Zingiber officinale*): A review", Journal of Medicinal Plants Research vol. 6(26), Jul. 11, 2012, pp. 4255-4258.

Moreira, Keila A, "Quantification, Antioxidant and Antimicrobial Activity of Phenolics Isolated from Different Extracts of Capsicum frutescens (*Pimenta malagueta*)", Molecules 19(4), Apr. 2014, pp. 5434-5447.

Nagao, Tomonori, et al., "A Green Tea Extract High in Catechins Reduces Body Fat and Cardiovascular Risks in Humans", Obesity, vol. 15, No. 6, Jun. 6, 2007, pp. 1473-1483.

Naveed, Muhammad, et al., "Chlorogenic acid (CGA): A pharmacological review and call for further research", Biomedicine & Pharmacotherapy, vol. 97, Jan. 2018, pp. 67-74.

Ohmori, Reiko, et al., "Antioxidant activity of various teas against free radicals and LDL oxidation", Lipids, 40 (8), Mar. 2005, pp. 849-853.

Onakpoya, Ij, et al., "The effect of chlorogenic acid on blood pressure: a systematic review and meta-analysis of randomized clinical trials", Journal of Human Hypertension vol. 29, Jun. 19, 2014, pp. 77-81.

Ooi, Vincent E.C., et al., "Immunomodulation and anti-cancer activity of polysaccharide-protein complexes", Curr Med Chem. vol. 7(7), Jul. 2000, pp. 715-279.

Parvaiz, Muhammad, et al., "Medicinal Importance of *Glycyrrhiza glabra* L. (Fabaceae Family)", Global Journal of Pharmacology 8 (1): 08-13, Jan. 2014, pp. 8-13.

Patel, Seema, "Rose hips as complementary and alternative medicine: overview of the present status and prospects", Mediterranean Journal of Nutrition and Metabolism, vol. 6, No. 2, Dec. 28, 2012, pp. 89-97.

Rachh, P.R., et al., "Antihyperlipidemic Activity of Gymenma sylvestre R. Br. Leaf Extract on Rats Fed with High Cholesterol Diet", Int J Pharmacol, 1-4, 6(2), 2010, pp. 138-141.

Rajewska, Justyna, "Biologically active compounds of edible mushrooms and their beneficial impact on health", Postepy Hig Med Dosw (Online) 58, abstract, Oct. 5, 2004, 2 pages.

Ribas, Graziela S., et al., "L-carnitine supplementation as a potential antioxidant therapy for inherited neurometabolic disorders", Gene vol. 533, Issue 2, 10, Jan. 2014, pp. 469-476.

Sandoval, Manuel, et al., "Cat's claw inhibits TNFα production and scavenges free radicals: role in cytoprotection.", Free Radical Biology and Medicine, vol. 29, Issue 1, Jul. 1, 2000, pp. 71-78., Jul. 1, 2000, pp. 71-78.

Saneja, Ankit, et al., "*Gymnema sylvestre* (Gurmar): A Review", Scholars Research Library Der Pharmacia Letter, 2 (1) (http://scholarsresearchlibrary.com/archive.html)., 2010, pp. 275-284.

Satdive, R.K., et al., "Antimicrobial activity of Gymnema sylvestre leaf extract", Fitoterapia, vol. 74, issues 7-8,, Dec. 2003, pp. 699-701.

Schütz, Katrin, et al., "Taraxacum—A review on its phytochemical and pharmacological profile", Journal of Ethnopharmacology vol. 107, Issue 3, Oct. 11, 2006, pp. 313-323.

Seals, Douglas R., et al., "Physiological geroscience: targeting function to increase healthspan and achieve optimal longevity", J Physiol. 594(8), 2015, pp. 2001-2024.

Senanayake, S.P.J. Namal, "Green tea extract: Chemistry, antioxidant properties and food applications—A review", Journal of Functional Foods vol. 5, Issue 4, Oct. 2013, pp. 1529-1541.

Shamtsyan, Mark, et al., "Immunomodulating and anti-tumor action of extracts of several mushrooms", J Biotechnol. 113(1-3), Sep. 30, 2004, pp. 77-83.

Shang, Ruiping, et al., "Effective dosing of L-carnitine in the secondary prevention of cardiovascular disease: a systematic review and meta-analysis", BMC Cardiovascular Disorders, vol. 14, Article No. 88, 2014, 7 pages.

Shukla, Hraddha, et al., "CoQ10 a super-vitamin: review on application and biosynthesis", Biotech vol. 8, Article No. 249, May 9, 2018, pp. 1-19.

Sliva, Daniel, "Cellular and physiological effects of *Ganoderma lucidum* (Reishi)", Mini Rev Med Chem. 4(8), Oct. 2004, 4 pages.

Stohs, Sidney J., et al., "A review of Natural Stimulant and Non-stimulant Thermogenic Agents", Phytotherapy Research vol. 30, issue 5, Feb. 2016, pp. 732-740.

Tajik, Narges, et al., "The potential effects of chlorogenic acid, the main phenolic components in coffee, on health: a comprehensive review of the literature", European Journal of Nutrition, vol. 56, Issue 7, Apr. 2017, pp. 2215-2244.

Udani, Jay K., et al., "Lowering the glycemic index of white bread using a white bean extract", Nutrition Journal, Oct. 28, 2009, 8 pages.

(56) References Cited

OTHER PUBLICATIONS

Udani, Jay, et al., "Systematic Review and Meta-Analysis of a Proprietary Alpha-Amylase Inhibitor from White Bean (*Phaseolus vulgaris* L.) on Weight and Fat Loss in Humans", Foods, 7(4), 63, 2018, 10 pages.
US-HHS, "Cat's Claw", NIH, National Center for Complementary and Integrative Health (updated May 2020), Nov. 29, 2016, 4 pages.
Vaidya, S., "Reviewon Gymnema: An Herbal Medicine for Diabetes Management", Pharmacia, vol. 1, Issue 2, Jul. 2011, pp. 37-42.
Vaiserman, Alexander, et al., "Anti-aging pharmacology: Promises and pitfalls. Ageing Research", Aging Research Reviews, vol. 31, Nov. 2016, pp. 9-35.

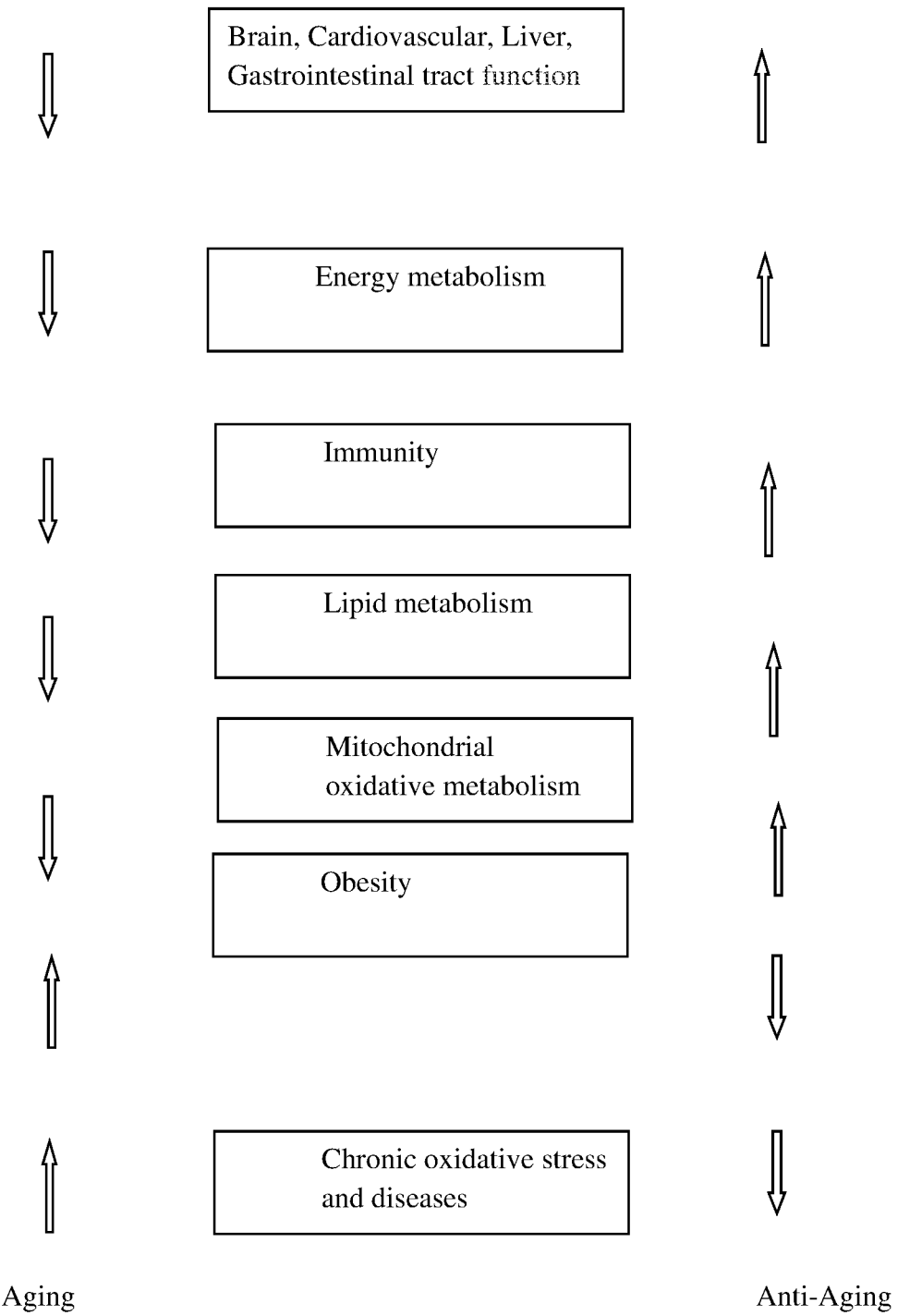
Figure 1. Some Aging Challenge Problems And Strategies On Anti-aging.

Figure 2. Summary Of The Main Anti-aging Effects Of Nutraceuticals
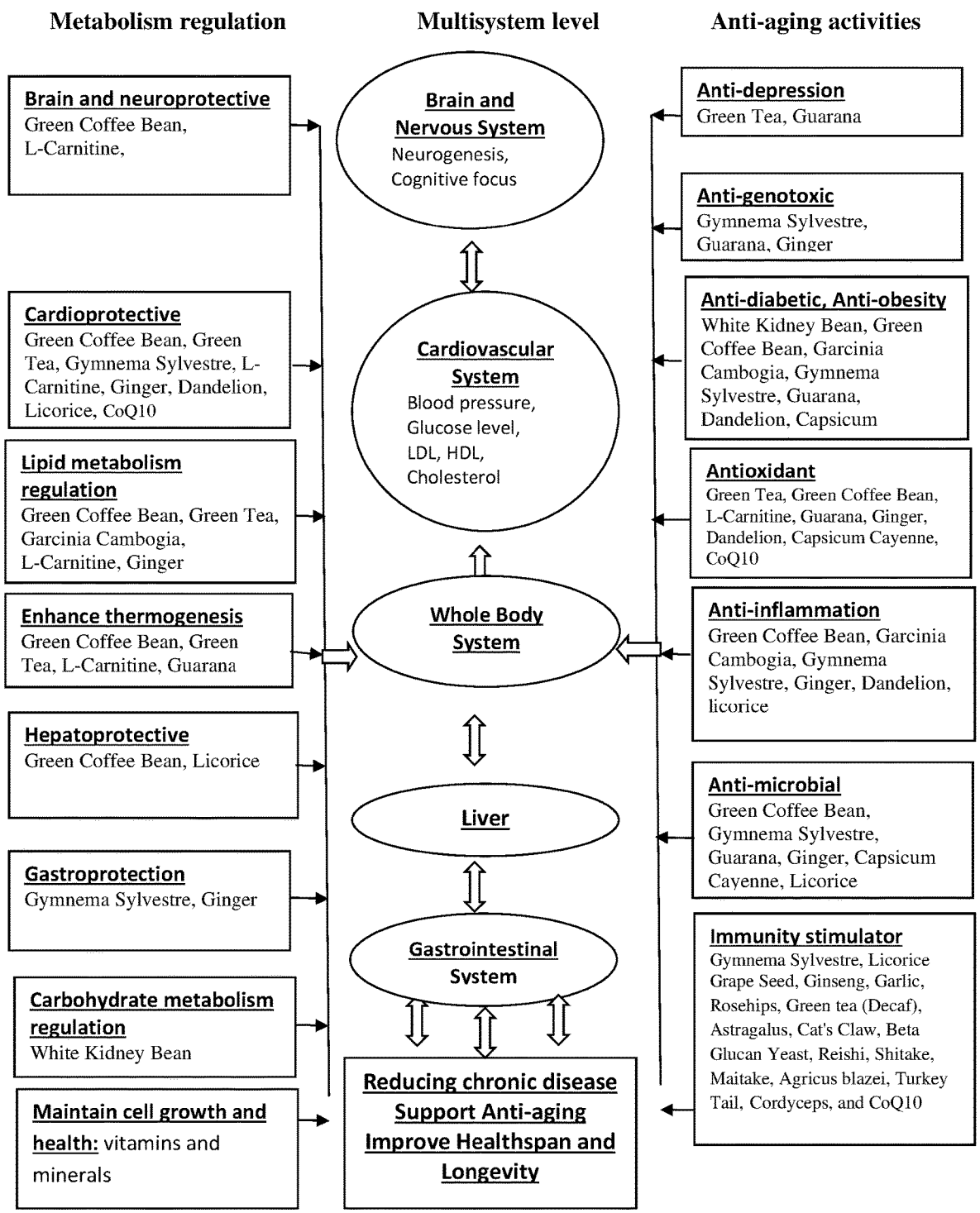

NUTRACEUTICALS SUPPLEMENT COMPOSITION FOR REGULATING METABOLISM AND ANTI-AGING

CROSS REFERENCE TO RELATED APPLICATIONS

This application is related to and claims priority of U.S. provisional application application no. 62/990,855 filed on Mar. 17, 2020. The Provisional Application is hereby incorporated by reference in its entirety. The priority of this application is expressly claimed, and the disclosure is hereby incorporated by reference in their entirety.

BACKGROUND OF THE INVENTION

Aging is the progressive biological change in an organism that leads to an increased risk of debility, disease, and death. With aging, some physiological functions of organs are deleterious changes and resemble those occurring in disease conditions such as hypertension, hyperlipidemia, chronic coronary disease, cardiovascular disease, cancer and diabetes. Those diseases can be correlated with several aging-associated conditions. As the result of significant improvements in hygiene, education, medicine, healthy diet, lifestyle, and health care, the proportion of aged people is steadily increasing. Healthspan extension is a key objective, which is the achievement of optimal longevity with good health and quality of life. Anti-aging studies are gaining wide attention for their focus change from simply prolonging lifespan to increasing health span, which emphasizes quality of life.

There are many aging management goals with proposed interventions such as reduction of internal toxicity and polluted environmental influences, inclusion of appropriate exercise and stress mediation, and hormonal therapies, as well as dietary interventions such as adherence to nutrition maximization, glycation control, calorie restriction mimetic and anti-aging nutrient supplements. Other approaches in anti-aging pharmacology are the use of medications and drugs for treating various pathological conditions related to aging. Among them are metformin, statins, beta-blockers, thiazolidinediones, newer generation β-adrenergic receptor inhibitors, renin-angiotensin-aldosterone system inhibitors, as well as anti-inflammatory medications that appear to be the most promising drug candidates. One problem is that these substances are not used currently for treating age-related pathological conditions in the absence of clinical manifestations of illness, though they could, theoretically, become agents for preventing or treating other syndromes or conditions commonly associated with aging. Many of these substances were developed for the treatment of acute medical conditions and consist of engineered molecules and specially synthesized compounds that are not known in nature. For this reason, many of these compounds require extensive testing and regulatory approval processes that are focused on identifying safety and efficacy for the treatment of one particular condition. Because many of the conditions associated with aging are chronic, long-term degenerative conditions, these compounds are difficult or impossible to test in this context.

In addition, there are numerous anti-aging therapy approaches including the investigation of genomic instability, epigenetic deregulation, loss of proteostasis, mitochondrial dysfunction, cellular senescence, exhaustion of stem cells, inflammation, telomere shortening, autophagy, impaired stress resistance and deregulated nutrient signaling, methylation and other forms of epigenetic chemical modification to nucleotides, DNA replication and gene expression improvement at the cell level. These novel therapeutic strategies are being developed and the most promising among them are stem cell and gene therapy. However, due to insufficient knowledge regarding the potential side effects and safety of these technologies, general public and medical professionals are still concerned about their safety and effectiveness for longtime use. Moreover, because many of these phenomena have not been accurately correlated to clinical conditions associated with aging, identifying particular modifications at the level of the genome has not been accurately correlated with the observable manifestations of aging.

Medicinal herbs have been widely applied in different disease stages for prevention and intervention stages. Medicinal herb supplements have shown their multi-target properties and allow them to be potential anti-aging interventions in the prevention and treatment of aging-associated disorders. Therefore, the use of more traditional medicinal/pharmacological interventions can be considered as a reasonable alternative and a holistic approach in anti-aging research[1,2,3]. Moreover, many of these compounds have a long history of use by humans to treat a variety of chronic conditions and have well-established safety profiles in long-term use.

Herbal medicine has a long history of application in anti-age and anti-disease treatment. It is believed that many of the medicinal herbs have anti-aging properties. Dietary and natural food supplements are widely used by individuals for potential health benefits such as reduction in total cholesterol or low-density lipoprotein cholesterol (LDL-C), and reducing risk of cardiovascular disease. Knowing that it is essential to maintain high levels of antioxidants, hormonal precursors, and other agents, which decrease with age, supplementing and replenishing these agents is a main factor in the development of anti-aging products. Studies have shown that some medicinal herbs are effective in the intervention or prevention of aging-associated disorders, and can be assigned the term "nutraceutical". Nutraceuticals can refer to a particular supplement or individual chemicals which are present in common foods, herbs or plants. A large number of nutraceuticals are beneficial phytonutrients. Phytonutrients are plant-based compounds that are generally considered to have a beneficial effect on health. Many nutraceuticals have been accepted to be beneficial because of their presumed safety and potential nutritional and therapeutic effects for anti-aging[1,2,3].

A large body of scientific evidence shows that nutritional supplementation can increase fat metabolism. There are several lipolytic supplements available on the market. Those natural ingredients, such as caffeine, green tea extract, L-carnitine, *Garcinia cambogia* (hydroxycitric acid), capsaicin, *ginseng*, taurine, silk peptides and octacosanol, all of which have shown scientific evidence of enhancing fat metabolism associated with improving endurance performance[4].

Controlled clinical trials show that Low Glycemic Index (GI) diets can lower cholesterol, improve blood sugar control, and insulin sensitivity in diabetics, and control body weight. A dietary supplement derived from the common white kidney bean (*Phaseolus vulgaris*) has been shown to inhibit alpha-amylase, the complex carbohydrate digesting enzyme. White kidney bean extract can effectively reduce the Glycemic Index (GI) of existing foods without modifying their ingredient profile. With the appropriate dose and formulation, the GI of white bread was significantly decreased by the addition of white bean extract in powder form. The inhibition of alpha-amylase may result in the lowering of the effective Glycemic Index (GI) of certain foods[5, 10].

The effects of catechins and epigallocatechin gallate (EGCG) on energy, lipid metabolism and cardiovascular disease have been examined in humans. The trials/research show that green tea extract high in catechins can reduce body fat and cardiovascular risks in humans. The results show that a greater decrease in systolic blood pressure (SBP), Low-density lipoprotein (LDL) cholesterol and decreases in body weight, body mass index, body fat ratio, body fat mass, waist circumference, hip circumference, visceral fat area, and subcutaneous fat area, were found in the catechin group compared with the control group. No adverse effect was found[6].

Chlorogenic acid (CGA) is the major hydroxycinnamic acid derivative present in green coffee beans. Human and animal studies have shown that chlorogenic acid and green coffee bean extracts (45-55% chlorogenic acid) enhance energy metabolism and expenditure, decrease blood lipid levels, improve glucose tolerance, and support weight management without cardiovascular effects. CGAs-enriched green coffee extracts have been postulated to decrease glucose absorption in the intestines, and modulate the activities of hepatic and pancreatic lipases actions, which could lead to an inhibition of fat accumulation and stimulation of lipid metabolism. CGA could modulate blood pressure possibly by promoting the effects of nitric oxide and by reducing blood homocysteine levels. CGAs have been demonstrated to have antioxidant activity by their ability to scavenge free radicals in vitro and increase the antioxidant capacity of plasma in vivo. The evidence from published RCTs suggests that CGA from green coffee bean intake causes statistically significant reductions in systolic and diastolic blood pressures[7,8,9].

The administration of Gymnema *Sylvestre* leaf extracts have been found to show reduction in elevated serum triglyceride (TG), total cholesterol (TC), very low-density lipoprotein (VLDL) and low-density lipoprotein (LDL) cholesterol in dose dependent manner. The efficiency of this agent was almost similar to that of a standard lipid lowering agent clifibrate[11]. In addition to hypolipidemic activity, extract of G. *Sylvestre* leaves showed good antimicrobial activity against *Bacillus pumilis, B. subtilis, Pseudomonas aeruginosa* and *Staphylococcus aureus*[12]. Anti-Inflammatory activity and free radical scavenging activity was found from extract of G. *Sylvestre* leaves. The inhibitory effects of DPPH radicals and LDL oxidation were found with aqueous extract of G. *sylvestre*[13].

An epidemiological study (637 elderly >60 years of age) evaluated the associations of metabolic disorders and anthropometric and biochemical biomarkers of lipid, glucose and oxidative metabolism and the habitual ingestion of guaraná (*Paullinia cupana*, Mart. Var. sorbilis) by an elderly population. The case-controlled study found that those who habitually drank guarana (GI, n=421) exhibited lower waist circumference and lower cholesterol (total and LDL-c) levels. Additionally, a significant association was found between lower levels of advanced oxidative protein product (AOPP) and habitual guaraná consumption. A low prevalence of various metabolic disorders was associated with guaraná ingestion. The prevalence of hypertension, obesity and metabolic syndrome in the GI group was lower than the prevalence found in the control group. The results constitute the epidemiological study to suggest a potentially protective effect of habitual guaraná ingestion against metabolic in elderly subjects. The studies on phytochemicals, including Guarana (*Paullinia cupana*) seeds extract and vitamin B1 and vitamin B3, showed benefits to enhance metabolism, antioxidant activities and energy, and showed no adverse influence on protein, lipid and carbohydrate profiles[14,15,16].

The researchers suggest that diet-induced hypercholesterolemic atherosclerosis is associated with an increase in oxidative stress. Dandelion root and leaf could protect against oxidative stress-linked atherosclerosis and decrease the atherogenic index. The results show that dandelion reduced the extent of atherosclerosis by reducing oxidative stress and serum TC, TG, LDL-C and raising serum HDL-C. Dandelion is beneficial in preventing hypercholesterolemic atherosclerosis and reducing risk factors for coronary artery disease[17,18].

The combinations of herbal ingredients to enhance thermogenesis are reported. The addition of the flavonoids naringin and hesperidin enhance the non-stimulant thermogenic effect of p-synephrine. The combination of carotenoids and isoflavones with other thermogenic agents, caffeine with p-synephrine, offers great potential to enhance and facilitate energy metabolism, suggesting an enhanced thermogenic effect.

The immune system is the human body's defense mechanism that can distinguish itself from foreign pathogens to protect the host from invasion and infection. Mushrooms have a long history as a health food that has been used in medicine for treatment of the immune system. The ability of mushrooms to modulate immune functions and inhibit tumor growth is mainly contributed to their extracts or bioactive compounds, including polysaccharides, glycopeptide/protein complexes (polysaccharide-peptide/protein complexes), cordycepic acid, proteoglycans, proteins and triterpenoids. Mushroom polysaccharides in particular (1→3)-β-D-glucans and their peptide/protein derivatives are most extensively studied for their immunomodulatory and antitumor activities. Scientific studies have demonstrated that the 1,3 form of Beta Glucan, polysaccharides found in mushrooms possesses remarkable abilities to support both innate and adaptive immunity, including the enhancement of T-Cell and natural killer cell (NK) activity. The immune system consists of the innate and adaptive immunity. Because mushrooms and their bioactive compounds are related to their effects on immune effector cells, they can have immune responses both in the innate and adaptive immunity. The immune effector cells include hematopoietic stem cells, lymphocytes, macrophages, dendritic cells (DCs), NK cells, and T cells. The underlying mechanism mainly involves the interaction of membrane receptors in the immune cells with the mushroom polysaccharides, especially β-D-glucans that triggers a cascade of signaling pathways and cytokine release to activate the human immune cells[19,20,21,22,23].

Vitamins, minerals, and a range of other nutrients can deliver significant anti-aging benefits. Some of the most potent benefits of anti-aging therapies include efforts to minimize the risk of age-related diseases, maintain healthy blood pressure and reduce the risk of heart disease, improve health at a cellular level, combat oxidative stress, neutralize free radicals that cause oxidative damage and lead to cellular deterioration, support the immune system, and aid energy production. Vitamins that help with anti-aging include vitamins A, C, D, E, K, B3, B5, B6, B9, etc. Minerals that help with anti-aging include Ca, Mg, K, Se, Cr, Ze, Fe, etc[24].

Oxidative stress is involved in the pathophysiology of a number of inherited metabolic disorders. It plays an important role in various diseases that show a high worldwide prevalence, such as cancer, rheumatoid arthritis, asthma, diabetes, cardiovascular and neurodegenerative diseases, including atherosclerosis, Alzheimer's disease, and other age-related degenerative disorders. However, the clinical use of classical antioxidants in these diseases has been poorly evaluated and so far only minimal benefit has been demonstrated. The antioxidative and antimicrobial properties of many plant extracts are of great interest as natural additives. There is a growing tendency to replace synthetic antioxidants with natural antioxidative and antimicrobial agents of plant extracts.

Although there are many phytoconstituents that could combat health problems that are widely prevalent such as diabetes and obesity, a few of these phytoconstituents could simultaneously help as anti-aging therapies. In addition, a lot of thermogenic agents (such as high concentrations of ephedrine and caffeine) are applied, which can act through stimulation of the central nervous system, but may have adverse cardiovascular effects. Therefore there is increasing interest, and a great demand for, a new combination of herbal ingredients, vitamins and minerals, including natural antioxidants, natural anti-inflammatories, natural immunity stimulators and non-stimulatory thermogenic agents, that have safe health benefits such as cardiovascular protective, neuro and brain protective, hepatic protective, and gastrointestinal protective effects.

SUMMARY OF THE INVENTION

The present invention is methods and compositions to improve overall health and specifically to promote the reduction of biochemical mechanisms underlying the aging process. The compositions are formulated from the ingredients, and specific forms, derivatives, and relative quantities and/or concentrations to have a wide range of potential health benefits based in part on the us of these specific formulations of together with other compounds, such as specifically identified and other species phytochemicals that provide a non-pharmacological, non-invasive approach and non-stimulant nutraceuticals for treatment or prevention of some chronic diseases and anti-aging and may be currently administered over time without concerns of toxicity, long-term safety, cumulative side effects that may be associated with other pharmaceutical compounds.

The term "nutraceutical" was created from a combination of the words "nutrition" and "pharmaceutical" in 1989 by Stephen DeFelice, Md. A nutraceutical is any substance that may be considered a food, or part of a food, that provides medical or health benefits, including the prevention and/or treatment of a disease. Such products may range from isolated nutrients, dietary supplements and diets to genetically engineered "designer" foods, herbal products and processed foods. The nutraceutical in this present invention is based on herbal extracts and substances that were approved to contain effective phytochemicals and phytochemical activities. The compositions in the present invention also contain other dietary supplements such as vitamins, minerals, coenzymes, and amino acids having a synergistic effect with the phytochemical constituents to provide a therapeutically effective dosage of a composition having antiaging properties.

The compositions and methods of present invention areis designed to satisfy the anti-aging related needs of the growing aging population and purposes to improve a person's health and increase their healthspan by enhancing brain and cardiovascular system protection, maintain the normal function of the liver and gastrointestinal system, enhancing metabolism of energy, lipid, and carbohydrates, regulating mitochondrial oxidative metabolism, and preventing and decreasing obesity and chronic oxidative stress and diseases.

This design is best presented in the FIG. 1, "Some aging challenge problems and strategies on anti-aging".

The present invention is based on therapeutic targets for anti-aging treatment with a combination of the following approaches:
(1) Natural antioxidant and anti-microbial supplement treatment to reduce free radical-induced damage, and chronic inflammatory diseases/disorders.
(2) Natural immunity supplement treatment to increase body defense systems.
(3) Natural phytochemicals in a well selected combination to provide multiple functions to maintain health with beneficial effects and safety More specifically, the present invention provides both a novel nutraceutical "Composition A" and a novel "Composition B." Both Composition A and Composition B contain a selection of effective phytochemicals and other beneficial compounds that provide safe pharmacological actions and health benefits and may be administered either alone, sequentially or in combination as described below. The ingredients and compositions may optimize biological and pharmacological effects of the following select ingredients and may be practically used as a natural and safe food additive to replace the synthetic antibiotics and chemicals, and thereby reduce the high medicinal cost and incidence of side effects. The recitation of a specific identified set of compositions grouped within either of the defined Composition A or Composition B is open-ended and is not meant to preclude the addition of additional compositions within the scope of either of Composition A or Composition B, including combinations thereof within either set and substitutions for synonyms, analogues, or derivatives thereof as described herein except as specifically defined and claimed herein.

More specifically, substances and/or their derivatives which may be used in the Composition A include, but are not limited to: White Kidney Bean Extract Powder, Green Tea Extract Powder, Green Coffee Bean Extract Powder, *Garcinia Cambogia* Extract Powder, Gymnema *Sylvestre* Extract Powder, L-Carnitine, Guarana Extract Powder, Ginger Root Powder, Dandelion Root Powder, *Capsicum* Cayenne Powder, Licorice Root Powder, Ascorbic Acid, d-Calcium Pantothenate Powder, Pyridoxine HCl Powder, Potassium Chloride, Magnesium Carbonate, and Chromium Yeast Powder, analogues thereof and compositions thereof and not to the exclusion of other compounds.

Substances and/or their derivatives which may be used in the Composition B include, but are not limited to: Grape Seed Extract Powder, *Ginseng* Extract Powder, Garlic Extract Powder, Rosehips Extract Powder, Green tea Extract (Decaf) Powder, *Astragalus* Extract Powder, Cat's Claw Extract Powder, Beta Glucan Yeast Powder, Reishi Extract Powder, Shitake Extract Powder, Maitake Extract Powder, Agricus blazei Extract Powder, Turkey Tail Extract Powder, *Cordyceps* Extract Powder, and CoQ10, analogues thereof and compositions thereof and not to the exclusion of other compounds.

DESCRIPTION OF THE TABLES AND FIGURES

Table 1. Major Plant Phytochemicals And Their Pharmacological Actions.

Table 2. Some Vitamins, Minerals, Other Agents And Their Health

FIG. 1 is an assembly of aging challenges and problems and selected individual and collective strategies to counter the aging process.

FIG. 2 is a summary of the main anti-aging effects of nutraceuticals.

DETAILED DESCRIPTION OF THE INVENTION

The Compositions and individual components that comprise Composition A and Composition B are described in Tables 1 and Table 2 below, together with the major phytochemical constituents of each component, and the non-exclusive list of the potential pharmacological actions that can be attributed to each individual or combination of phytochemicals within the individual component.

TABLE 1

Major Plant Phytochemicals And Their Pharmacological Actions

| Herbal plants | Major phytochemicals | Pharmacological actions |
| --- | --- | --- |
| White kidney bean | α-amylase inhibitors protein (α-AI). | Carbohydrate blocker or starch neutralizer, low glycemic index (GI), anti-diabetes, glucose metabolism regulation, weight management, reduce abdominal fat. |
| Green tea | Catechins, EGCG-polyphenols | Antioxidant, anticancer, antiaging, antiproliferant, antistress, enhancing thermogenesis, delay lipid oxidation, cardioprotective. |
| Green coffee bean | Chlorogenic acid | Antioxidant, anti-inflammatory, anti-diabetic, anti-cancer, anti-obesity, antibacterial, hepatoprotective, cardioprotective, antipyretic, neuroprotective, antiviral, anti-microbial, anti-hypertension, free radicals scavenger, a central nervous system (CNS) stimulator, non-stimulant thermogenic substances, modulate lipid metabolism & glucose metabolism. |
| Garcinia cambogia | Hydroxycitric acid (HCA), | Increased fat oxidation, anti-obesity, hypolipidemic, antidiabetic, anti-inflammatory, anticancer, anthelmintic, anticholinesterase and hepatoprotective activities. |
| Gymnema Sylvestre | Gymnemic-Acid Gymnemic-Acid-B | Antiflu, antihistaminic, anti-inflammatory, antiobesity, antipyretic, antiseptic, hypolipidemic activity, anti-microbial, antiviral, Cyclooxygenase-inhibitor, fungicide, gastrostimulant, hypotensive, hypothermic, immunostimulant, sedative, serotoninergic, thyrotropicM. |
| Guarana | Polyphenols and catechins, caffeine, | Antidepressant, antioxidant, carcinogenesis, antigeniotoxic, antibacterial effects, reduce risk of obesity and metabolic syndrome and thermogenic agent. |
| Ginger | Gingerol, shogaol | Anti-ulcer, anti-inflammatory, cardiovascular effects, anticancer, anticoagulant, antiemetic, antioxidant, gastrointestinal effects, modulate lipid metabolism, anti-arthritic, antimicrobial activities and antigenotoxic. |
| Dandelion | Sesquiterpene, taraxacoside, phenolic, flavonoids | Diuretic, choleretic, anti-inflammatory, anti-oxidative, anti-carcinogenic, analgesic, anti-hyperglycemic, anti-coagulatory and prebiotic effects. |
| Capsicum cayenne | Capsaicinoids/capsaicin | Antimicrobial activities, antioxidant, anti-diabetes, anti-obesity, non-stimulant thermogenic substances. |
| Licorice | Glycyrrhizic acid | Anti-inflammatory, antiviral, antimicrobial, antioxidative, anticancer activities, immunomodulatory, hepatoprotective and cardioprotective effects. |
| Grape Seed | Proanthocyanidins | Antioxidative, anti-inflammatory, antimicrobial, cardioprotective, hepatoprotective, neuroprotective effects. |
| Ginseng (*Panax Ginseng*) | Ginsenosides | Modulates blood pressure, metabolism and immune functions, antimicrobial and antifungal. |
| Garlic | Allicin | Enhance immunities, reduce cardiovascular diseases and cancer risk, antioxidant, antimicrobial, enhancement of detoxification and hepatoprotection. |
| Rosehips (*Rosa canina*) | polyphenols, essential fatty acids, vitamin A and C, mineral Ca and Fe | Antioxidant, antiarthritic, anti-inflammatory, analgesic, antidiabetic, cardioprotective, antimicrobial, immunomodulatory, gastroprotective and skin ameliorative. |
| Astragalus | Polysaccharide astragalosides isoflavonoids | Strengthen the immune system and reduce inflammation, treat fatigue. |
| Cat's claw | Oxindole | Strengthen the immune system, anti-cancer, anti-inflammatory. |
| Green tea (Decaf) | EGCG | Antioxidant, anticancer, antiaging, antiproliferant, antistress. |

TABLE 2

Some Vitamins, Minerals, Other Agents And Their Health Benefits

| Vitamins, Minerals[24], and others | Name | Health Benefits |
| --- | --- | --- |
| Vitamin C | Ascorbic Acid | May lower the risk for some cancers (e.g. mouth, esophagus, stomach, and breast cancer), may protect against cataracts. Helps make collagen, helps make the neurotransmitters serotonin and norepinephrine. Acts as an antioxidant, neutralizing unstable molecules that can damage cells. Bolsters the immune system. |

TABLE 2-continued

Some Vitamins, Minerals, Other Agents And Their Health Benefits

| Vitamins, Minerals[24], and others | Name | Health Benefits |
|---|---|---|
| Vitamin B5 | d-Calcium Pantothenate | Helps convert food into energy. Helps make lipids (fats), neurotransmitters, steroid hormones, and hemoglobin. |
| Vitamin B6 | Pyridoxine HCl | Aids in lowering homocysteine levels and may reduce the risk of heart disease. Helps convert tryptophan to niacin and serotonin, a neurotransmitter that plays key roles in sleep, appetite, and moods. Helps make red blood cells. Influences cognitive abilities and immune function. |
| Potassium Chloride | Potassium | Balances fluids in the body. Helps maintain steady heartbeat and send nerve impulses. Needed for muscle contractions. Seems to lower blood pressure. Getting enough potassium from your diet may benefit bones. |
| Potassium Chloride | Chloride | Balances fluids in the body. A component of stomach acid, essential to digestion. |
| Magnesium Carbonate | Magnesium | Needed for many chemical reactions in the body. Works with calcium in muscle contraction, blood clotting, and regulation of blood pressure. Helps build bones and teeth. |
| Chromium Yeast | Chromium (organic Cr) | Enhances the activity of insulin, helps maintain normal blood glucose levels, free energy from glucose. |
| L-carnitine | L-carnitine titration acetyl-L-carnitine | Lipid metabolism regulation, antioxidant, cardioprotective, enhancing energy, brain protective. |
| CoQ10 | Ubiquinone | Increase energy, boost immunity, support muscle and bone strength, regulating blood sugar, and maintain brain health and significantly improve heart health. |
| Mushrooms Reishi, Shitake, Maitake, Agricus blazei, Turkey Tail, Cordyceps | Beta Glucan, Polysaccharides, Cordycepic Acid | Enhance immunity, anti-aging. |

White Kidney Bean (*Phaseolus vulgaris*) extract is a preferred natural source of α-amylase protein (α-A1) inhibitors. The α-amylase inhibitor from white kidney beans inhibits the mammalian α-amylase and thus reduces carbohydrate metabolism and lowers the estimated GI (eGI) of high-GI food. Low glycemic index (GI) foods are particularly effective for diabetics to help keep their blood sugar levels under control. Low GI diets decrease the risk of developing type II diabetes and coronary heart disease, lower cholesterol, improve blood sugar control (HbA1c) and insulin sensitivity in diabetics, delay the return of hunger and decrease body weight in adolescents[5,10]. White kidney bean (*Phaseolus vulgaris* L) used in the present invention is preferably extracted from seeds by water and ethanol extraction and has a characteristic chemical composition when extracted by the water and ethanol extraction method. The daily dosage for the present invention is from about 150 to about 900 mg, preferably between about 400 mg 750 mg, approximately and most preferably 600 mg of white kidney bean (*Phaseolus vulgaris* L) extract.

Green tea (*Camellia sinensis*) leaves is a preferred natural source of several polyphenolic components, including catechins. Catechins him of are a class of low molecular weight polyphenols including catechin (C), catechin gallate (CG), gallocatechin (GC), gallocatechin gallate (GCG), epicatechin (EC), epicatechin gallate (ECG), epigallocatechin (EGC), and epigallocatechin gallate (EGCG). Among these, epigallocatechin-3-gallate (EGCG) is the most bioactive and the most scrutinized component. Numerous studies of catechins' antioxidant and anti-cancer action, anti-angiogenesis, antiaging properties, and their preventive effects on ischemic heart disease have verified its functions. Catechins can reduce body fat, cholesterol levels, and blood pressure. Green tea extract can also be used in lipid-bearing foods to delay lipid oxidation and to enhance the shelf-life of various food products. The anine in green tea may play a role in reducing stress. Synergistic properties of green tea extracts with other sources of polyphenolic constituents are increasingly recognized as being potentially important to the medicinal benefits.[25,26] Green tea extracts exhibit stimulant thermogenic activity while producing clinically insignificant increases in heart rate and blood pressure because of a combination of mechanisms. In the present invention, green tea (*Camellia sinensis*) is extracted from tea leaves by water extraction. Extraction contains 50-55% of tea polyphenols, 30-35% of total catechins, and 15-20% EGCG. The caffeine concentration is limited to no more than 5% in green tea extract. The daily dosage for the present invention is from about 100 to about 600 mg preferably between 250 and 500 mg, and most preferably approximately 400 mg of green tea extract.

Green coffee bean (*Coffea arabica*) is unroasted coffee beans which are a preferred natural source of Chlorogenic acid (CGA), a biologically active dietary polyphenol. It is a major and important component in green coffee bean. Phenolic acids have recently gained substantial attention due to their various practical, biological and pharmacological effects. Chlorogenic Acid (CGA, 3-CQA) is the most abundant isomer among caffeoylquinic acid isomers (3-, 4-, and 5-CQA). Many basic and clinical research studies have shown its effect for reduction of risk for a variety of diseases, e.g. diabetes, cardiovascular disease (CVD), obesity, cancer, and hepatic steatosis. In addition, it has been found that CGA could modulate lipid and glucose metabolism in both genetically and healthy metabolic related disorders. The wide range of potential health benefits of CGA provides a non-pharmacological and non-invasive approach for treatment or prevention of some chronic diseases and anti-aging[27]. In the present invention, CGA derived from Green coffee bean (Coffee arabica) is extracted from bean seed by water extraction. Extraction contains 45-55% of Chlorogenic acid (CGA). The daily dosage for the present invention is from about 50 to about 300 mg, preferably between about 150 and 250 mg, and most preferably approximately 200 mg of green coffee bean (Coffee arabica) extract.

Garcinia cambogia extract is a preferred natural source of hydroxycitric acid (HCA), a main organic acid component. This active ingredient can block fat and suppress the appetite. fat HCA increases oxidation and exhibits anti-obesity activity because it inhibits a key enzyme, citrate lyase, which the body needs to make fat from carbohydrates. It also suppresses appetite by increasing serotonin levels; low serotonin levels are associated with depression and emotional or reactive eating. The HCA extract from the Garcinia cambogia also exerts hypolipidaemic, antidiabetic, anti-inflammatory, anticancer, anthelmintic, anticholinesterase and hepatoprotective activities[4,28,52]. In the present invention, Garcinia cambogia is extracted from bean seed by water extraction. Extraction contains 45-55% of hydroxycitric acid (HCA). The daily dosage for the present invention is from about 100 to about 600 mg preferably between about 200 and about 500 mg, and most preferably approximately 400 mg of Garcinia cambogia extract.

Gymnema Sylvestre (Gymnema Sylvestre) is an herb distributed throughout the world. The leaves of Gymnema Sylvestre (Gymnema Sylvestre) for a preferred natural source of triterpene saponins belonging to oleanane and dammarene classes. Oleanane saponins are gymnemic acids and gymnemasaponins, while dammarene saponins are gymnemasides. The other chemical constituents are flavones, anthraquinones, hentri-acontane, pentatriacontane, á and â-chlorophylls, phytin, resins, d-quercitol, tartaric acid, formic acid, butyric acid, lupeol, â-amyrin related glycosides and stigmasterol, some alkaloids, betaine, choline, and anthroquinones. Gymnemic acid is the main active chemical constituent isolated from the Gymnema Sylvestre plant. The leaves of the plant are widely used for the treatment of diabetes and as a diuretic. The plant is documented to possess beneficial effects as digestive, anti-inflammatory, diuretic, hypoglycemic and antihelmentic, antidiabetic, anti-obesity, hypolipidaemic, antimicrobial, and free radical scavenging. It is believed to be used in dyspepsia, constipation, jaundice, haemorrhoids, cardiopathy, asthma, bronchitis and leucoderma [11,12,13,28,29,30]. In this present invention the constituent components of Gymnema Sylvestre (Gymnema Sylvestre) are extracted from leaves by water extraction. Extraction contains 20-30% of gymnemic acids. The daily dosage for present invention is from about 50 to about 300 mg, preferably between about 100 and 250 mg, and most preferably 200 mg of Gymnema Sylvestre (Gymnema Sylvestre) extract.

L-carnitine is a naturally occurring amino acid derivative and naturally occurring essential cofactor of several enzymes (carnitine translocase, acylcarnitine transferases I and II). L-carnitine is found in body, foods and most supplements. It plays a crucial role in the production of energy by transporting fatty acids into cells' mitochondria, which act as engines within cells, burning these fats to create usable energy. Besides its important role in the metabolism of lipids, L-carnitine is also a potent antioxidant (free radical scavenger) and thus may protect tissues from oxidative damage. Research illustrates the potential benefits of carnitine's different forms, which may be used for various conditions, including heart and brain diseases. Some animal and human studies suggest that acetyl-L-carnitine may help prevent age-related mental decline and helps reverse the decline in brain function associated with Alzheimer's and other brain diseases. Since L-carnitine can easily cross the blood-brain barrier, L-carnitine supplementation may also be beneficial in preventing neurological damage derived from oxidative injury. In addition, L-carnitine supplementation has been shown to have favorable effects in CVD patients[31,32,33]. In the present invention, L-carnitine is 99% pure L-carnitine (titration). The daily dosage for the present invention is from about 30 to about 180 mg preferably between about 75 and 150 mg, and most preferably approximately 120 mg of L-carnitine.

Guarana (Paullinia cupana) seeds are a preferred natural source of methylxanthine derivatives, including caffeine, theophylline and theobromine. It also contains a high proportion of polyphenols and catechins. Based on its broad spectrum of medicinal effects, Guarana is currently used for its antidepressant, antioxidant, chemoprophylactic properties in carcinogenesis and antigenotoxic activity, and antibacterial effects, and has been demonstrated to reduce risk of obesity and metabolic syndrome. Guarana is classified as a thermogenic agent because of its caffeine contents[15]. In the present invention, Guarana (Paullinia cupana) is extracted from seed by water and ethanol extraction. Extraction contains 15-22% of caffeine. The daily dosage for the present invention is from about 20 to about 120 mg, preferably between about 50 and about 100 mg and most preferably approximately 80 mg of Guarana (Paullinia cupana) extract.

Ginger (Zingiber Officinalis) is a species included in the Zingiberaceae family. The active ingredients in ginger include volatile ginger oils (e.g. sesquiterpenes, sesquiterpenoids bisapolene, zingiberene, monoterpenoid and zingiberol). The primary pungent agents (phenylalkylketones or vanillyl ketones) of ginger are gingerol, and other gingerol analogues such as the shogoals, paradol and zingerone. The major pharmacological activity of ginger appears to be due to gingerol and shogaol. The gingerols have analgesic, sedative, antipyretic and antibacterial effects. Ginger is one of the most commonly used spices and widely used medicinal plants. It has been demonstrated to improve diet induced metabolic abnormalities. Based on various studies, ginger has shown health benefits such as anti-ulcer, anti-inflammatory, cardiovascular effects, anticancer, anticoagulant, anti-emetic effects, antioxidant, gastrointestinal effects, lipid effects, anti-arthritic effect, antimicrobial activities and antigenotoxic activity[34,35]. In the present invention, Ginger (Zingiber Officinalis) is extracted from root by water extraction. Extraction contains gingerol and shogaol. The daily dosage for the present invention is from about 12 to about 72 mg preferably between about 35 and 60 mg, and most preferably approximately 48 mg of Ginger (Zingiber Officinalis) extract.

Dandelion (Taraxacum officinale) root extract is a preferred natural source of high concentrations of sesquiterpenes, Saponins, flavonoids, alkaloids, and phenols. Several flavonoids (e.g., caffeic acid, chlorogenic acid, luteolin, and luteolin 7-glucoside), more than five sesquiterpene lactones and thirteen benzenoids/phenolic compounds have been isolated from the root of dandelion. Other constituents of dandelion root include various triterpenes and phytosterols such as taraxasterol and ψ-taraxasterol, as well as their acetates and their 16-hydroxy derivatives arnidol and faradiol, α- and β-amyrin, β-sitosterol, and stigmasterol. Moreover, dandelion roots contain carbohydrates (e.g., inulin), carotenoids (e.g., lutein), fatty acids (e.g., myristic acid), minerals, sugars (e.g., fructose, glucose, sucrose), vitamins, choline, mucilage, and pectin. Dandelion has been known since ancient times for its curative properties and has been utilized in folk medicine for the treatment of various diseases such as dyspepsia, heartburn, spleen and liver disorders, hepatitis and anorexia, inflammation and breast and uterus cancers. This medicinal plant has been shown to favorably affect choleretic, antirheumatic and diuretin properties, anti-inflammatory, anti-oxidative, anti-carcinogenic, analgesic, anti-hyperglycemic, anti-coagulatory and prebiotic effects. It is also acclaimed as a nontoxic herb with exceptional values for its antioxidant and anti-inflammatory properties[17,18,36]. In the present invention, Dandelion (*Taraxacum officinale*) is extracted from root by water extraction. Extraction ratio is 4:1. Extraction contains sesquiterpenes, saponins, flavonoids, alkaloids, and phenols. The daily dosage for the present invention is from about 5 to about 30 mg, preferably between 10 and about 25 mg and most preferably approximately 20 mg of Dandelion (*Taraxacum officinale*) extract.

*Capsicum* cayenne pepper (*Capsicum frutescens*) is a household vegetable that has been consumed as a food and as a medical plant and is a preferred natural source of phenolic compounds, flavonoids, carotenoids, and vitamin C. The most commonly occurring capsaicinoids in cayenne are capsaicin (69%), dihydrocapsaicin (22%), nordihydrocapsaicin (7%), homocapsaicin (1%), and homodihydrocapsaicin (1%). Capsaicin (8-methyl-N-vanillyl-6-nonenamide) is an active component in Cayenne pepper that is ahydrophobic, and a highly pungent compound. A number of research studies have shown multiple pharmacological effects of capsaicin on a variety of physiological systems such as the cardiovascular system (acts against high cholesterol levels), gastro-intestinal tract, regulate metabolic rate, pain relief, and reduce the symptoms of peripheral neuropathy (post-herpetic neuralgia caused by shingles). It has shown benefits for antimicrobial and antioxidant activities, anti-diabetes (lower plasma glucose levels) and anti-obesity [37,38]. In this present invention, *Capsicum* cayenne pepper (*Capsicum frutescens*) is extracted from fruit by water extraction. Extraction contains 30,000 to 60,000 SHU of capsaicin and dihydrocapsaicin. The daily dosage for the present invention is from about 10 to about 60 mg, preferably about 25 to about 50 mg and most preferably approximately 40 mg of *Capsicum* cayenne pepper (*Capsicum frutescens*) extract.

Licorice (*Glycyrrhiza glabra* L) has long been used worldwide as an herbal medicine and natural sweetener. For thousands of years licorice has been used for medicinal purposes including indigestion and stomach inflammation, cough suppression, ulcer treatment, hepatitis C, and pulmonary and skin diseases. Licorice root contains glycyrrhizic acid, triterpene saponins, flavonoids, isoflavonoids and chalcones. Glycyrrhizic acid is believed to be the main biologically active component. Clinical and experimental studies suggest that it has several useful pharmacological properties such as anti-inflammatory (including anti-NLRP-3 inflammasome), antiviral, antimicrobial, antioxidative, anticancer activities, immunomodulatory, hepatoprotective and cardioprotective effects[39,40]. In the present invention, Licorice (*Glycyrrhiza glabra* L) is extracted from root by water extraction and has a characteristic chemical profile when extracted by this method. Extraction ratio is 4:1 and contains sesquiterpenes, saponins, flavonoids, alkaloids, and phenols. The daily dosage for the present invention is from about 5 to about 30 mg, between about 10 and about 25 mg, and most preferably about 20 mg of Licorice (*Glycyrrhiza glabra* L) extract.

Vitamins and minerals are considered essential nutrients—because they perform hundreds of roles in the body. They help shore up bones, heal wounds, and bolster the immune system. They also convert food into energy and repair cellular damage. A varied health diet generally provides enough of each vitamin and mineral. However, some people (such as elderly, chronically ill) may need supplements to correct deficiencies of particular vitamins or minerals. Vitamins and minerals used in the present invention include, but not limited to, ascorbic acid, potassium chloride, magnesium carbonate, d-calcium pantothenate, chromium yeast, and pyridoxine HCl. The detailed health benefits are described in table 2[24]. The daily dosage for the present invention is from about 10 to about 60 mg and most preferably 40 mg of ascorbic acid, from about 10 to about 60 mg and most preferably 40 mg of potassium chloride, from about 10 to about 60 mg and most preferably 40 mg of magnesium carbonate, from about 0.9 to about 5.4 mg and most preferably 3.6 mg of d-calcium pantothenate (92%), from about 30 to about 180 mg and most preferably 120 mg of chromium yeast (2000 ppm chromium), from about 0.8 to about 4.8 mg and most preferably 3.2 mg of pyridoxine HCl.

Grape (*Vitis Vinifera* L) seed extract is a preferred natural source of proanthocyanidins, flavonoids, polyphenols, anthocyanins, procyanidines, and the stilbene derivative resveratrol. Grape seed extract in particular has been reported to possess a broad spectrum of pharmacological and therapeutic effects such as antioxidative, anti-inflammatory, and antimicrobial activities, as well as having cardioprotective, hepatoprotective, and neuroprotective effects [41]. In the present invention, Grape (*Vitis Vinifera* L) is extracted from seed by water and ethanol extraction. Extraction contains 90-98% of proanthocyanidins. The daily dosage for the present invention is from about 40 to about 240 mg, preferably between about 100 and about 200 mg, and most preferably approximately 60 mg of Grape (*Vitis Vinifera* L) seed extract.

Ginseng (*Panax Ginseng*) is commonly used either by itself or in combination with other medicinal ingredients as a key herb in Chinese medicine. Ginseng (*Panax Ginseng*) extract contains ginsenosides and therapeutic potential of ginsenosides, which has been studied extensively. Ginsenosides are triterpene saponins, which are the pharmacologically active components in *ginseng*. Numerous research studies have proven that *ginseng* and ginsenosides are involved in modulating multiple physiological activities, including modulating blood pressure, metabolism and immune functions and antimicrobial and antifungal[42]. In the present invention, Ginseng (*Panax Ginseng*) is extracted from leaves and stem by water and ethanol extraction and exhibits a characteristic distribution of constituents when extracted by this method. Extraction ratio is 20:1 and contains 25-35% of Ginsenosides. The daily dosage for the present invention is from about 25 to about 150 mg, preferably between about 50 and about 75 mg, and most preferably approximately 100 mg of Ginseng (*Panax Ginseng*) extract.

Garlic (*Allium sativum* L) is widely used either by itself or in combination with other medicinal ingredients. Garlic extract is a preferred natural source of allicin, 1-propenyl allyl thiosulfonate, allyl methyl thiosulfonate, (E,Z)-4,5,9-trithiadodeca-1,6,11-triene 9-oxide (ajoene), and y-L-glutamyl-S-alkyl-L-cysteine. Among those, allicin has played important dietary and medicinal roles. Several experimental and clinical investigations suggest many favorable effects of garlic including enhancement of immunities, reduction of risk factors for cardiovascular diseases, reduction of cancer risk, antioxidant effect, antimicrobial effect, and enhancement of detoxification of foreign compounds and hepatoprotection[43]. In the present invention, Garlic (*Allium sativum* L) is extracted from bulb by water extraction. Extraction contains 0.2-0.4% of allicin. The daily dosage for the present invention is from about 50 to about 300 mg, preferably between about 150 and about 250 mg, and most preferably approximately 200 mg of Garlic (*Allium sativum* L) extract.

Rosehips (*Rosa canina*) has been developed as a functional food due to its nutraceutical and pharmaceutical benefits. It is rich in polyphenols, essential fatty acids, vitamin A and C, and the minerals Ca and Fe. The extracts have demonstrated antioxidant, antiarthritic, antiinflammatory, analgesic, antidiabetic, cardioprotective, antimicrobial, immunomodulatory, gastroprotective and skin ameliorative effects[44]. In the present invention, Rosehips (*Rosa canina*) is extracted from fruit by water extraction and has a characteristic distribution of constituents when extracted from deferred by this method. The daily dosage for the present invention is from about 10 to about 60 mg, preferably between about 30 and about 50 mg, and most preferably approximately 40 mg of Rosehips (*Rosa canina*) extract.

*Astragalus* root has a long history as an herbal supplement, which is used in treating the common cold, seasonal allergies, heart conditions, kidney disease, chronic fatigue and more. The root extraction contains many active plant compounds, which are believed to be responsible for its benefits such as helping to strengthen the immune system and reduce inflammation[45,51]. In the present invention *Astragalus* (*Astragalus membranaceus*) is extracted from root by water extraction with extraction ratio of 4:1 and exhibits a characteristic distribution of constituents when extracted by this method. The daily dosage for the present invention is from about 50 to about 300 mg, preferably between about 150 and 250 mg and most preferably approximately 200 mg of *Astragalus* (*Astragalus membranaceus*) extract.

Cat's claw (*Uncaria tomentosa*) bark and root have been used for centuries by South Americans as a remedy for arthritis and to treat digestive disorders such as gastritis, colitis, and stomach ulcers. Cat's claw is a preferred natural source of a compound known as pentacyclic oxindolic alkaloid (POA) that is believed to have anti-inflammatory effects such as tumor necrosis factor-alpha (TNF-alpha). TNF-α helps regulate the immune response and apoptosis in old or damaged cells[46, 47] In the present invention, Cat's claw (*Uncaria tomentosa*) is extracted from inner bark by water extraction with extraction ratio of 10-15:1 and exhibits a characteristic formulation and trace elements from the inner bark characteristic of the water extraction method. The extraction contains 3-5% of Oxindole. The daily dosage for the present invention is from about 12.5 to about 75 mg preferably between about 40 and about 60 mg, and most preferably approximately 50 mg of Cat's claw (*Uncaria tomentosa*) extract.

Mushrooms and Beta Glucan Yeast are applied in the present invention, which contains Reishi extract, Shitake extract, Maitake extract, Agricus blazei extract, Turkey Tail extract, *Cordyceps* extract and Beta Glucan Yeast extract. These mushrooms have been shown to support a number of aspects of healthy immune function, including the enhancement of T-Cell and Natural Killer Cell activity. This combination of mushrooms provides strong immune support due to its high concentration of 1,3 Beta Glucan, Polysaccharides, Cordycepic Acid, vitamins and minerals and more health components[19-23,48,49]. The mushrooms extraction used in the present invention are including, but not limited to, Reishi (*Ganoderma Lucidum*) extract 4:1, Shitake (*Lentinus edodes*) extract 18:1, Maitake (*Grifola Frondosa*) extract 4:1, Agricus blazei (*Agricus blazei Murill*) extract 4:1, Turkey Tail (*Trametes versicolor*) extract 16:1, and *Cordyceps* (*Cordyceps sinensis*) extract. Extracts contain about 10-25% of polysaccharides, 10-25% of Beta Glucan, 7-10% of Cordycepic acid, which are extracted from fruiting body or mycelium (*Cordyceps*) by water and ethanol extraction and exhibit a characteristic distribution of active constituents when extracted by the water and ethanol method. Beta Glucan Yeast in the present invention contains 20-25% of Beta glucans. The daily dosage for the present invention is from about 63 to about 660 mg, preferably between about 100 and about 500 mg and most preferably between approximately 252-440 mg of mushroom extracts and Beta Glucan Yeast.

Coenzyme Q10 (CoQ10) is found in the biological system and has numerous functions in the human. Coenzyme Q10 supplementation increases body energy production in the form of ATP and helps to treat various human diseases such as cardiomyopathy, muscular dystrophy, periodontal disease, etc. There are two different forms of CoQ10: Ubiquinol and Ubiquinone. Ubiquinol is the reduced antioxidant form, and ubiquinone is the oxidized form. The present invention is using Ubiquinone, which has been proven to help increase energy, boost immunity, support muscle and bone strength, regulate blood sugar, and maintain brain health and significantly improve heart health. In the present invention, Coenzyme Q10 (CoQ10, ubiquinone) is 98-100% pure form of ubiquinone. The daily dosage for the present invention is from about 30 to about 180 mg, preferably between about 75 and about 150 mg, and most preferably approximately 120 mg of Coenzyme Q10 (CoQ10, ubiquinone).

To prepare the components of the invention, each of the active ingredients is combined in intimate admixture with a suitable carrier and excipient according to desired physical characteristics such as powder flowing ability, tableting ability, capsuling ability, compressibility, and the like.

When admixed, all components of the compositions of the present invention are in a solid, granular form. This form aids in the manufacturing process in that it tends not to clump or stick to the machinery in which it is admixed. The granular solid is freely divided, free-flowing, dry, and may be easily handled.

In preparing the compositions in oral dosage form, oral solids (e.g., powder, tablets, pills, and capsules) carriers such as microcrystalline cellulose, maltodextrin, starch, diluents, granulating agents, lubricants, binders, disintegrating agents, anti-caking agents and the like may be employed. The amount of those non active ingredients employed in the present invention composition A is from about 10% to about 25% of the total mass, most preferably from about 15% to 20% of the total mass of compositions of the present invention. The amount of those non active ingredients employed in the present invention composition B is from about 20% to about 60% of the total mass, most preferably from about 40% to 50% of the total mass of compositions of the present invention. To the extent that other compounds equivalent to the identified species in either of Composition A or Composition B may separately be allocated to either of the listed Composition sets, then the relative percentages and identities of the foregoing compounds could be altered accordingly without departing from the present description provided herein.

To make the compositions of the present invention, all components are blended. Prior to their blending, all components are preferably maintained in sealed containers in which they are protected from atmospheric humidity. The components may be combined and blended in standard commercial scale blenders such as a 100-1000 kg Ribbon blender. The components are blended in the blender for a period of time sufficient to assure intimate admixture of all, such period of time depending on the amount of material to be admixed and the size of the blender.

The compositions of the present invention, when in this stable, granular form, may be diluted preferably in water or juice and then consumed. A proper dosage range of the compositions of the present invention in humans will depend upon the particular needs of the mammal, and may range from about 0.775 g to about 4.65 g per day, and preferably about 1.55-3.10 g per day for the Composition A, and may range from about 0.65 g to about 3.9 g per day, and preferably about 1.3-2.6 g per day for the Composition B. In its solid granular form, the Compositions A and B of the present invention may be diluted preferably in water or juice and then consumed. A dose of mentioned composition of the present invention may be diluted in about 200-250 ml of water.

The compositions of the present invention, when in the tablet or capsule form, may be consumed directly with water or other liquid. A proper dosage range of the compositions of the present invention in humans will depend upon the particular needs of the mammal and may range from about 1 tablet/capsule to about 6-8 tablets/capsule per day, and preferably about 2-4 tablets/capsules per day for the Composition A, and may range from about 1 tablet/capsule to about 6-8 tablet/capsule per day, and preferably about 4-6 tablets/capsules per day for the Composition B. A dose of one tablet/capsule of the composition of the present invention may contain 750 to 790 mg of solid granular form for Composition A, and 630 to 670 mg of solid granular form for Composition B.

The compositions of the present invention, when in tablet or capsule or granule form, may be consumed 1-3 tablets/capsules/servings of Composition A in the early morning and 1-3 tablets/capsules/servings of Composition A at noontime, mid-day, then 2-4 tablets/capsules/servings of Composition B may be consumed in the afternoon, then 2-4 tablets/capsules/servings of Composition B before the bed time.

The invention will now be illustrated by reference to the following examples and do not limit the invention in any fashion.

Example 1

Each serving (0.775 gram) of Composition A contains Part A including all active ingredients White Kidney Bean Extract Powder 150 mg, Green Tea Extract Powder 100 mg, Green Coffee Bean Extract Powder 50 mg, *Garcinia Cambogia* Extract Powder 100 mg, Gymnema *Sylvestre* Extract Powder 50 mg, L-Carnitine 30 mg, Guarana Extract Powder 20 mg, Ginger Root Powder 12 mg, Dandelion Root 5 mg, *Capsicum* Cayenne Powder 10 mg, Licorice Root Powder 5 mg, Ascorbic Acid 12 mg, d-Calcium Pantothenate Powder 0.91 mg, Pyridoxine HCl Powder 0.73 mg, Potassium Chloride 12.1 mg, Magnesium Carbonate 12.2 mg, and Chromium Yeast Powder 27.5 mg; Part B including all other ingredients such as microcrystalline cellulose.

The above ingredients in Part A were blended, pulverized as needed. Then, the above ingredients in Part B were blended and screened with Part A. Mix containing Part A and Part B were combined into a blender and blended for 15 minutes. After mixing well, the dry powder was screened using a Sifter and the screened materials were discharged into double poly-lined drums, which were then sealed such that they are airtight and stored in a cool and dry place. The completed mix can be granulated, tableted or encapsulated. One to two servings (0.775 grams to 1.55 grams) of completed Composition A can be consumed with 200 ml of water and consumed in the morning, and another one to two servings (0.775 grams to 1.55 grams) of completed Composition A can be consumed with 200 ml of water and consumed at noontime, mid-day.

Example 2

Each serving (0.775 gram) of Composition A contains Part A including all active ingredients White Kidney Bean Extract Powder 150 mg, Green Tea Extract Powder 100 mg, Green Coffee Bean Extract Powder 50 mg, *Garcinia Cambogia* Extract Powder 100 mg, Gymnema *Sylvestre* Extract Powder 50 mg, L-Carnitine 30 mg, Ginger Root Powder 14 mg, Dandelion Root 10 mg, *Capsicum* Cayenne Powder 12 mg, Licorice Root Powder 8 mg, Ascorbic Acid 20 mg, d-Calcium Pantothenate Powder 0.9 mg, Pyridoxine HCl Powder 0.73 mg, Potassium Chloride 12 mg, Magnesium Carbonate 12 mg, and Chromium Yeast Powder 28 mg; Part B including all other ingredient such as microcrystalline cellulose.

The above ingredients in Part A were blended, pulverized as needed. Then, the above ingredients in Part B were blended and screened with Part A. Mix containing Part A and Part B were combined into a blender and blended for 15 minutes. After mixing well, the dry powder was screened using a Sifter and the screened materials were discharged into double poly-lined drums, which were then sealed such that they are airtight and stored in a cool and dry place. The completed mix can be granulated, tableted or encapsulated. One to two servings (0.775 grams to 1.55 grams) of completed Composition A can be consumed with 200 ml of water and consumed in the morning, and another one to two servings (0.775 grams to 1.55 grams) of completed Composition A can be consumed with 200 ml of water and consumed at noontime, mid-day.

Example 3

Each serving (0.650 gram) of Composition B contains Part A including all active ingredients Grape Seed extract 50 mg, *Ginseng* extract 30 mg, Garlic extract 50 mg, Rosehips extract 20 mg, Green tea (Decaf) extract 30 mg, *Astragalus* extract 50 mg, Cat's Claw extract 15 mg, Beta Glucan Yeast extract 15 mg, Reishi extract 15 mg, Shitake extract 15 mg, Maitake extract 10 mg, Agricus blazei extract 10 mg, Turkey Tail extract 15 mg, *Cordyceps* extract 15 mg, and Coenzyme Q10 30 mg.

Part B including all other ingredients such as microcrystalline cellulose.

The above ingredients in Part A were blended, pulverized as needed. Then, the above ingredients in Part B were blended and screened with Part A. Mix containing Part A and Part B were combined into a blender and blended for 15 minutes. After mixing well, the dry powder was screened using a Sifter and the screened materials were discharged into double poly-lined drums, which were then sealed such that they are airtight and stored in a cool and dry place. The completed mix can be granulated, tableted or encapsulated. Two to four servings (1.3 grams to 2.6 grams) of completed Composition B can be consumed with 200 ml of water and consumed in the afternoon, and another two to four servings (1.3 grams to 2.6 grams) of completed Composition B can be consumed with 200 ml of water and consumed before bed time.

Example 4

Each serving (0.650 gram) of Composition B contains
Part A including all active ingredients Grape Seed extract 37.5 mg, *Ginseng* extract 25 mg, Garlic extract 50 mg, Rosehips extract 10 mg, Green tea (Decaf) extract 30 mg, *Astragalus* extract 50 mg, Cat's Claw extract 12.5 mg, Beta Glucan Yeast extract 12.5 mg, Reishi extract 7.5 mg, Shitake extract 7.5 mg, Maitake extract 2.5 mg, Agricus blazei extract 7.5 mg, Turkey Tail extract 12.5 mg, and *Cordyceps* extract 12.5 mg.
Part B including all other ingredients such as microcrystalline cellulose.

The above ingredients in Part A were blended, pulverized as needed. Then, the above ingredients in Part B were blended and screened with Part A. Mix containing Part A and Part B were combined into a blender and blended for 15 minutes. After mixing well, the dry powder was screened using a Sifter and the screened materials were discharged into double poly-lined drums, which were then sealed such that they are airtight and stored in a cool and dry place. The completed mix can be granulated, tableted or encapsulated. Two to four servings (1.3 grams to 2.6 grams) of completed Composition B can be consumed with 200 ml of water and consumed in the afternoon, and another two to four servings (1.3 grams to 2.6 grams) of completed Composition B can be consumed with 200 ml of water and consumed before bed time.

As between the various constituents of the individual compositions, the following list of compositions and extractions and derivatives thereof are considered critical components and may be formulated as subsets or critical components of a separate composition comprising Compound A and Compound B and individual subsets, blends, and assembled combinations of each Compound. The priority in creating a sub-combination of the foregoing constituents is to include elements and compound subsets selected from the individual and collective components of Great Seed extract, *Ginseng*, Astrialgalus, Cat's Claw, Beta glucan yeast, condryceps extract, and extraction constituents and formulations thereof.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

Other systems, devices, methods, features and advantages of the subject matter described herein will be or will become apparent to one with skill in the art upon examination of the following figures and detailed description. It is intended that all such additional systems, devices, methods, features and advantages be included within this description, be within the scope of the subject matter described herein, and be protected by the accompanying claims. In no way should the features of the example embodiments be construed as limiting the appended claims, absent express recitation of those features in the claims.

REFERENCES

PATENT DOCUMENTS

| Publication # | Date | Inventor |
|---|---|---|
| US2004/0001817 A1 | Jan. 1, 2004 | Vincent C. et al |
| US20050003027 | Jun. 1, 2005 | Diaz Jose A. Naranjo Eduardo M. |
| US20060024385 | Feb. 2, 2006 | Pedersen Mark A |
| 20080305096 | Nov. 12, 2008 | Verdegeram Peter. J. E. |
| 7,579,027 | Aug. 25, 2009 | Briketvedt |
| 20090252796 | Aug. 10, 2009 | Mazed Mohammad A., et al |
| EP 2617429 | Jul. 24, 2013 | Soga Satoko, et al |
| 8,563,051 | Oct. 22, 2013 | Samuel, et al |
| 8,974,841 | Oct. 3, 2015 | Qu, Shengbo |
| 9,931,316 | Apr. 3, 2018 | Paul Edward |

OTHER PUBLICATIONS

1. Alexander Vaisermanl and Oleh Lushchak. REVIEW Implementation of longevity-promoting supplements and medications in public health practice: achievements, challenges and future perspectives. J Transl Med (2017) 15:160 DOI 10.1186/s12967-017-1259-8.
2. Alexander M Vaiserman et al. Anti-aging pharmacology: Promises and pitfalls. Ageing Research Reviews Volume 31, November 2016, Pages 9-35.
3. Seals D R, Justice J N, LaRocca T J. Physiological geroscience: targeting function to increase healthspan and achieve optimal longevity. J Physiol. 2016; 594(8):2001-24.

4. Jisu Kim, Jonghoon Park, Kiwon Kim Nutrition Supplements to Stimulate Lipolysis: A Review in Relation to Endurance Exercise Capacity. J of Nutritional Science and Vitaminology 62.141-161. (2016).
5. Jay K Udani, Betsy B Singh, Marilyn L Barrett, Harry G Preuss. Lowering the glycemic index of white bread using a white bean extract. Nutrition Journal. December 2009, 8:52.
6. Tomonori Nagao, Tadashi Hase, Ichiro Tokimitsu. A Green Tea Extract High in Catechins Reduces Body Fat and Cardiovascular Risks in Humans. Obesity. 6 Sep. 2012. https://doi.org/10.1038/oby.2007.176.
7. IJ Onakpoyal, EA Spencer, MJ Thompson, and CJ Heneghan The effect of chlorogenic acid on blood pressure: a systematic review and meta-analysis of randomized clinical trials. *Journal of Human Hypertension* volume 29, pages 77-81(2015).
8. Muhammad Naveed et al. Chlorogenic acid (CGA): A pharmacological review and call for further research. Biomedicine & Pharmacotherapy Volume 97, January 2018, Pages 67-74.
9. Sidney J.et al. A review of Natural Stimulant and Non-stimulant Thermogenic Agents. Phytotherapy Research vol 30, issue 5, February 2016.
10. Jay Udani, Ollie Tan and Jhanna Molina Systematic Review and Meta-Analysis of a Proprietary Alpha-Amylase Inhibitor from White Bean (*Phaseolus vulgaris* L.) on Weight and Fat Loss in Humans. *Foods*. 2018, 7(4), 63.
11. P. R. Rachh, M. R. Rachh, N. R. Ghadiya, D. C. Modi, K. P. Modi, N. M. Patel, M. T. Rupareliya. Int J Pharmacol, 2010, 1-4.
12. R. K. Satdive, P. Abhilash, P. F. Devanand. Fitoterapia, 2003, 74,699-701.
13. R Ohmori, T Iwamoto, M Tago, T. Takeo, T. Unno, H Itakura. A comprehensive scientific overview of *Garcinia cambogia*. Lipids, 2005, 40 (8), 849-53.
14. Bulku E, Zinkovsky D, Patel P, Javia V, Lahoti T, Khodos I, Stohs J M, Ray SD (2010). A novel dietary supplement containing multiple phytochemicals and vitamins elevates hepatorenal and cardiac antioxidant enzymes in the absence of significant serum chemistry and genomic changes. Ox. Med. Cell. Longev. 3:129-144.
15. Lidihone Hamerski, Genise Vieira Somner and Neusa Tamaio Paullinia cupana Kunth (Sapindaceae): A review of its ethnopharmacology, phytochemistry and pharmacology Lidilhone. Journal of Medicinal Plants Research Review. Vol. 7(30), pp. 2221-2229, 10 August, 2013.
16. Krewer C D, Ribeiro E E, Ribeiro E A M, Moresco R N, da Rocha MIDM, Montagner GFFD, Machado M M, Viegas K, Brito E, da Cruz IBM (2011). Habitual Intake of Guarana and Metabolic Morbidities: An Epidemiological Study of an Elderly Amazonian Population. Phytother. Res. 25:1367-1374.
17. Marta Gonzalez-Castejón, Francesco Visioli, Arantxa Rodriguez-Casado.Diverse biological activities of dandelion. Nutrition Reviews, Volume 70, Issue 9, 1 Sep. 2012, Pages 534-547, https://doi.org/10.1111/j.1753-4887.2012.00509.x
18. Ung-Kyu Choi et al. Hypolipidemic and Antioxidant Effects of Dandelion (*Taraxacum officinale*) Root and Leaf on Cholesterol-Fed Rabbits. Int J Mol Sci, v.11 (1); 2010 January PMC2820990.
19. Cuixia Guo, Man-Wing Choi and Peter C-K Cheung Mushroom and Immunity, Current Topics in Nutraceutical Research. Vol. 10, No. 1, pp. 31-42, 2012.
20. Oliva D. Cellular and physiological effects of *Ganoderma lucidum* (Reishi). Mini Rev Med Chem. 2004 October; 4(8):873-9.
21. Ooi V E, Liu F Immunomodulation and anti-cancer activity of polysaccharide-protein complexes. Curr Med Chem. 2000 July; 7(7):715-29.
22. Mau J L, Lin H C, Chen C C. Antioxidant properties of several medicinal mushrooms. J Agric Food Chem. 2002 Oct. 9;50 (21):6072-7.
23. Rajewska J, Balasinska B. Biologically active compounds of edible mushrooms and their beneficial impact on health. Postepy Hig Med Dosw (Online). 2004 Oct. 5; 58:352-7.
24. List of vitamins. Harvard Health Publishing. Harvard Medical School. Updated: Nov. 14, 2018 Published: June, 2009.
25. S. P. J. Namal Senanayake. Green tea extract: Chemistry, antioxidant properties and food applications—A review. Journal of Functional Foods Volume 5, Issue 4, October 2013, Pages 1529-1541.
26. Raymond Cooper et al. Medicinal Benefits of Green Tea: Part I. Review of Noncancer Health Benefits. The Journal of Alternative and Complementary Medicine Vol. 11, No. 3.
27. Narges Tajik et al. The potential effects of chlorogenic acid, the main phenolic components in coffee, on health: a comprehensive review of the literature. European Journal of Nutrition. October 2017, Volume 56, Issue 7, pp 2215-2244.
28. Ruchi Badoni, Semwal Deepak, Kumar Semwalllze, Vermaak AlvaroViljoen. A comprehensive scientific overview of *Garcinia cambogia*. Fitoterapia. Volume 102, April 2015, Pages 134-148.
29. Ankit Sanejal, Chetan Sharma, K. R. Aneja, Rakesh Pahwal. Gymnema *Sylvestre* (Gurmar): A Review. Scholars Research Library Der Pharmacia Letter, 2010: 2 (1) 275-284 (http://scholarsresearchlibrary.com/archive.html).
30. Vaidya S. Review on Gymnema: An Herbal Medicine for Diabetes Management Dr. H. S.Gaur University, Sagar (M.P.).
31. Ruiping Shang et al. Effective dosing of L-carnitine in the secondary prevention of cardiovascular disease: a systematic review and meta-analysis. BMC Cardiovascular Disorders volume 14, Article number: 88 (2014).
32. Panel Graziela, S.Ribasab, Carmen R.Vargasabc, Moacir Wajnera Review L-carnitine supplementation as a potential antioxidant therapy for inherited neurometabolic disorders Gene Volume 533, Issue 2, 10 Jan. 2014, Pages 469-476.
33. Karen L. Goa and Rex N. Brogden. L-Carnitine A Preliminary Review of its Pharmacokinetics, and its Therapeutic Use in Ischaemic Cardiac Disease and Primary and Secondary Carnitine Deficiencies in Relationship to its Role in Fatty Acid Metabolism. *Drugs* volume 34, pages 1-24 (1987).
34. Mohammad Sharrif Moghaddasil and Hamed Haddad Kashani Journals Review Ginger (*Zingiber officinale*): A review. Journal of Medicinal Plants Research Vol. 6(26), pp. 4255-4258, 11 July, 2012 Academic.
35. Department of Pharmacy, School of Medical & Allied Sciences, Galgotias University Yamuna Expressway, Greater Noida, G. B Nagar, Uttar Pradesh. Ginger medical use and benefits. ejpmr, 2016,3(7), 127-135.

36. Katrin Schutz et al. *Taraxacum*—A review on its phytochemical and pharmacological profile Journal of Ethnopharmacology Volume 107, Issue 3, 11 Oct. 2006, Pages 313-323.
37. Kamon Chaiyasit M Sc. Pharmacokinetic and The Effect of Capsaicin in *Capsicum frutescens* on Decreasing Plasma Glucose Level. J Med Assoc Thai 2009; 92 (1): 108-13.
38. Keila A. Moreira et al. Quantification, Antioxidant and Antimicrobial Activity of Phenolics Isolated from Different Extracts of *Capsicum frutescens* (Pimenta Malagueta) Molecules 2014, 19(4), 5434-5447.
39. Marjan Nassiri Asl, et al. Review of Pharmacological Effects of *Glycyrrhiza* sp. and its Bioactive Compounds. Phytotherapy Research Volume 22, Issue 6, June 2008, Pages 709-724.
40. Khan Ahmadi M., Naghdi Badi H., Akhondzadeh S., Khalighi Sigaroodi F., Mehrafarin A., Shahriari S., Hajiaghaee R. A Review on Medicinal Plant of *Glycyrrhiza Glabra* L. Journal of Medicinal Plants May 2013, Volume 12, Number 46; Page(s) 1 To 12.
41. Marjan Nassiri-Asl Hossein Hosseinzadeh Review of the pharmacological effects of *Vitis vinifera* (Grape) and its bioactive compounds Phytotherapy: 12 Jan. 2009.
42. Kar Wah Leung et al. Pharmacology of ginsenosides: a literature review. *Chinese Medicine* volume 5, Article number: 20 (2010).
43. Leyla Bayan, Peir Hossain Koulivand, and Ali Gorji Garlic: a review of potential therapeutic effects. Avicenna J Phytomed. 2014 January-February; 4(1): 1-14.
44. Patel, Seema. Rose hips as complementary and alternative medicine: overview of the present status and prospects. Mediterranean Journal of Nutrition and Metabolism, vol. 6, no. 2, pp. 89-97, 2013.
45. Block K I, Mead M N. Immune system effects of *echinacea, ginseng*, and *astragalus*: a review. Integr Cancer Ther. 2003 September;2(3):247-67.
46. National Center for Complementary and Integrative Health. Cat's Claw. Updated Nov. 29, 2016.
47. G. Richard N. Fogoros, MD Health Benefits of Cat's Claw. Can the traditional Amazonian remedy treat arthritis? Medically reviewed. Updated on Jul. 17, 2019.
48. Shamtsyan M, Konusova V, Maksimova Y, Goloshchev A, Panchenko A, Simbirtsev A, Petrishchev N, Denisova N. Immunomodulating and anti-tumor action of extracts of several mushrooms. J Biotechnol. 2004 Sep. 30; 113 (1-3):77-83.
49. Cheung N K, Modak S, Vickers A, Knuckles B. Orally administered beta-glucans enhance anti-tumor effects of monoclonal antibodies. Cancer Immunol Immunother. 2002 November; 51(10):557-64. Epub 2002 Sep. 20. PMID: 12384807.
50. Hraddha Shukla, Kashyap Kumar Dubey.CoQ10 a super-vitamin: review on application and biosynthesis. Biotech vol 8, Article No: 249 (2018).
51. Wang S H, Wang W J, Wang X F, Chen W. [Effect of *Astragalus* polysaccharides and berberine on carbohydrate metabolism and cell differentiation in 3T3-L1 adipocytes]. Zhongguo Zhong Xi Yi Jie He Za Zhi. 2004 October;24(10):926-8. Chinese. PMID: 15553830.
52. Yun Jung Kim et al A mixture of the aqueous extract of *Garcinia cambogia*, soy peptide and L-carnitine reduces the accumulation of visceral fat mass in rats rendered obese by a high fat diet. Genes & Nutrition volume 2, pages 353-358(2008).

We claim:
1. A nutraceutical supplement comprising effective amounts of: white kidney bean extract powder, green tea extract powder, green coffee bean extract powder, *Garcinia cambogia* extract powder, L-carnitine, and *Guarana* extract powder.
2. The nutraceutical supplement of claim 1, further comprising an amount of a composition selected from the group consisting of: ginger root powder, dandelion root, capsicum cayenne powder, licorice root powder, ascorbic acid, d-calcium pantothenate powder, pyridoxine HCl powder, potassium chloride, magnesium carbonate, and chromium yeast powder, Gymnema *sylvestre* extract powder, and combinations thereof.
3. The nutraceutical composition of claim 2, wherein the ginger is from root and contains zingiberol and shogaol within the range of approximately 1.5-5 percent total mass of the ginger.
4. The nutraceutical composition of claim 2, wherein the dandelion root extract ratio is 3-4:1 and contains sesquiterpenes, saponins, flavonoids, alkaloids, and phenols, and combinations thereof, within the range of approximately 0.5-1 percent total mass of the dandelion.
5. The nutraceutical composition of claim 2, wherein the capsicum cayenne powder is extracted from fruit and contains 30,000-60,000 Scoville Heat Units (SHU) of capsaicin and dihydrocapsaicin within the range of approximately 1-2 percent total mass solid, dried capsicum cayenne.
6. The nutraceutical composition of claim 2, wherein the licorice root contains glycyrrhizic acid within the range of approximately 0.5-1 percent total mass of the licorice.
7. The nutraceutical composition of claim 2, wherein the Gymnema *sylvestre* extract powder is from leaves and contains 20-30% gymnemic acids within the range of approximately 5-10 percent of the total mass solid of the Gymnema *Sylvestre* extract powder.
8. The nutraceutical composition of claim 1, wherein the white kidney bean extract powder is from seeds obtained by a 10-15:1 extraction, and which contains a-amylase inhibitors protein within the range of approximately 10-25 percent total mass of the white kidney bean extract powder.
9. The nutraceutical composition of claim 1, wherein the green tea extract powder is from leaves and contains 50-55% of tea polyphenols, 30-35% of total catechins, and 15-20% EGCG within the range of approximately 12-20 percent total mass of the green tea extract powder.
10. The nutraceuticals composition of claim 1, wherein the green coffee extract powder is from seeds and contains 45-55% of chlorogenic acid (CGA), wherein the dry weight loss composition is within the range of approximately 5-10 percent of the total mass of the green coffee bean extract powder.
11. The nutraceutical composition of claim 1, wherein the Garcinia cambogia extract powder is from fruit and contains 45-55% hydroxycitric acid (HCA) in a quantity within the range of approximately 10-15 percent total mass of the Garcinia cambogia extract powder.
12. The nutraceutical composition of claim 1, wherein the L-carnitine contains 99% of L-carnitine.
13. The nutraceutical composition of claim 1, wherein the Guarana extract powder is from seeds and contains polyphenols and catechins and contains no more than 10-22% of caffeine and the polyphenols are within the range of approximately 2-5 percent total mass solid, dried *Guarana* seeds extract.
14. The nutraceutical composition of claim 1 further comprising water soluble vitamins selected from the group consisting of ascorbic acid (vitamin C), d-calcium pantoth- enate (vitamin B5), and pyridoxine (vitamin B6) within the range of approximately 1-2 percent total mass solid, ascorbic acid having 100% of vitamin C, in a quantity within the range of approximately 0.1-0.2 percent total mass solid, d-calcium pantothenate having 92% of vitamin B5, and in a quantity within the range of approximately 0.1-0.2 percent total mass solid, pyridoxine having 82% of vitamin B6.

15. The nutraceutical composition of claim 1, further comprising minerals include potassium chloride, magnesium carbonate, and chromium yeast, wherein the dry weight loss compositions suitable for health benefits, are in a quantity within the range of approximately 1.5-4 percent total mass solid, potassium chloride, in a quantity within the range of approximately 1.5-4 percent total mass solid, magnesium carbonate, and in a quantity within the range of approximately 3-5 percent total mass solid, chromium yeast having a concentration of about 2000 ppm Cr.

16. A nutraceuticals supplement comprising, as % total mass of total dietary composition effective amounts of grape seed, ginseng, garlic, rosehips, decaffeinated green tea, *Astragalus*, cat's claw, beta glucan yeast, reishi, shitake, maitake, *Agricus blazei*, turkey tail, cordyceps, and coenzyme Q10 (CoQ10) including analogs, derivatives, and combinations thereof.

17. The nutraceuticals composition of claim 16, wherein
the grape seed extract is *Vitis vinifera* containing 95% of proanthocyanidins,
the ginseng is *Panax ginseng* extract containing 30.0% ginsenosides;
the garlic is *Alliwn sativrun* L. extract containing 0.2% Allicin,
the rosehips is *Rosa canina* powder;
the green tea is a *Camellia Sinensis* decaffeinated extract containing 50% of ETGCG,
the *Astragalus* is *Astragalus membranaceus* extract 5:1,
the cat's claw is *Uncaria toinentosa* extract containing 3.0% oxindole;
the yeast is beta glucan yeast containing 20% of glucans,
the reishi mushroom is *Ganoderma lucidum* extract 4:1;
the shitake is *Lentinus edodes* extract 18:1 containing 10% polysaccharides,
the maitake is *Grifola frondosa* extract 4:1,
the *Agricus blazei* is *Agaricus Blazei Murill* extract 4:1,
the turkey tail is *Trametes versicolor* extract 16:1, containing 25% polysaccharides,
the cordyceps is *Cordyceps sinensis* extract containing 7% of cordycepic acid, and
the Coenzyme Q10 is Ubidecarenone containing 98-100% of CoQ10, and combinations thereof.

18. The nutraceutical composition of claim 16, where the composition is a dry weight-loss composition suitable for immunity support, anti-inflammatory, antimicrobial, antioxidation, and anti-aging which is in a quantity within the range of approximately percent total mass solid, dried grape seed extract 5-10%, ginseng extract 3-6%, garlic extract 7-12%, rosehips extract 1-4%, green tea extract 5-10%, *Astragalus* extract 7-10%, cat's claw extract 2-5%, beta glucan yeast extract 2-5%, reishi extract 1-5%, shitake extract 1-5%, maitake extract 0.5-2%, *Agricus blazei* extract 1-5%, turkey tail extract 2-5%, *Cordyceps* extract 1-5%, and CoQ10 4-8%, and combinations thereof.

19. The nutraceutical composition of claim 16, wherein (i) the daily dosage for the composition is one to six servings, respectively 0.775 grams to 4.65 grams; (ii) one to two servings, respectively 0.775 grams to 1.55 grams of the composition, is consumed with 200 ml of water in the morning; and (iii) another one to two servings, respectively 0.775 grams to 1.55 grams of the composition, is consumed with 200 ml of water at noontime or mid-day.

20. The nutraceuticals composition of claim 16, wherein (i) daily dosage for the composition is two to eight servings, respectively 1.3 grams to 5.2 grams; (ii) wherein two to four servings respectively 1.3 grams to 2.6 grams the composition are consumed with 200 ml of water in the afternoon; and (iii) and another two to four servings respectively 1.3 grams to 2.6 grams of the composition are consumed with 200 ml of water before bed time.

\* \* \* \* \*